US00PP24330P2

(12) United States Plant Patent
Korlipara

(10) Patent No.: US PP24,330 P2
(45) Date of Patent: Mar. 18, 2014

(54) ***ECHINACEA* PLANT NAMED 'FERRIS WHEEL'**

(50) Latin Name: *Echinacea purpurea*
Varietal Denomination: Ferris Wheel

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 60 days.

(21) Appl. No.: 13/573,339

(22) Filed: Sep. 11, 2012

(51) Int. Cl.
*A01H 5/00* (2006.01)

(52) U.S. Cl.
CPC ..... *A01H 5/00* (2013.01)
USPC ..... Plt./428

(58) Field of Classification Search
CPC ..... A01H 5/00; A01H 4/00; A01H 1/00; A01H 1/04; A01H 1/06
USPC ..... Plt./428
See application file for complete search history.

*Primary Examiner* — Annette Para
(74) *Attorney, Agent, or Firm* — Klarquist Sparkman, LLP

(57) ABSTRACT

A new and distinct *Echinacea* plant named 'Ferris Wheel' characterized by large inflorescences with quilled ray florets of creamy white, a compact, narrow, multicrown habit, a long bloom time, and excellent vigor.

1 Drawing Sheet

Botanical denomination: *Echinacea purpurea.*
Variety designation: 'Ferris Wheel'.

BACKGROUND OF THE INVENTION

The present invention relates to a new and distinct cultivar of *Echinacea purpurea* and given the cultivar name 'Ferris Wheel'. *Echinacea* is in the family Asteraceae. This new cultivar is a seeding originating from a planned breeding program to make a quilled series of compact *Echinacea*. The exact parents of this selection are unknown, unnamed, proprietary plants.

Compared to *Echinacea* 'Quills and Thrills' (U.S. Plant Pat. No. 23,241), the new cultivar has creamy white flowers rather than purple pink.

This new *Echinacea* cultivar is distinguished by:

1. large inflorescences with quilled ray florets of creamy white,
2. a compact, narrow, multicrown habit,
3. a long bloom time, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old plant of *Echinacea* 'Ferris Wheel' growing in the in the trial field in full sun in early July in Canby, Oreg. A black background was held behind the plant to show it more clearly.

FIG. 2 shows a close up of the flower on the same plant.

DETAILED PLANT DESCRIPTION

The following is a detailed description of the new *Echinacea* cultivar based on observations of two-year-old specimens growing in the trial field in full sun in early July in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition.

Plant:

*Type*.—Herbaceous perennial.
*Hardiness*.—USDA Zones 4 to 9.
*Size*.—Grows to about 35 cm wide and 63 cm tall to top of inflorescences.
*Form*.—Basal clump, with about 19 stems from the ground.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 1 to 3 inflorescences per stem.
*Size*.—To 60 cm tall to a terminal inflorescence and 1 cm wide at base.
*Internode length*.—2 cm to 6 cm.
*Surface texture*.—Strigose.
*Color*.—Yellow Green 147C.

Leaf (basal):

*Type*.—Simple.
*Shape*.—Ovate.
*Arrangement*.—Basal.
*Blade size*.—Grows to 13.5 cm long and 8 cm wide.
*Margins*.—Coarsely serrate.
*Apex*.—Acute.
*Base*.—Attenuate.
*Surface texture*.—Strigose on both sides.

*Venation*.—Pinnate, with 3 main veins from the base, Yellow Green 147D on top and bottom side.

*Color*.—Topside Green N137A, bottom side closest to Yellow Green 147B.

*Petiole description*.—Clasping, grows to 17 cm long and 4 mm wide above the clasp, sparsely strigose, Yellow Green 147D.

Leaf (stem):

*Type*.—Simple.

*Shape*.—Lanceolate.

*Arrangement*.—Alternate.

*Blade size*.—Grows to 11.5 cm long and 5 cm wide.

*Margins*.—Serrate.

*Apex*.—Acuminate.

*Base*.—Attenuate.

*Surface texture*.—Strigose on both sides.

*Venation*.—Pinnate, with 3 main veins from the base, Yellow Green 137C on top and Yellow Green 137D on bottom side.

*Color*.—Topside Green 137A, bottom side closest to Yellow Green 147B.

*Petiole description*.—On all but upper leaves, clasping, grows to 4.5 cm long and 4 mm wide above the clasp, sparsely strigose, Yellow Green 137C.

Inflorescence:

*Type*.—Composite on terminal stalked heads.

*Number of flowering stems from the ground*.—About 19.

*Flowering stem*.—Grows to 61 cm tall from the base of the plant to the terminal inflorescence and can grow to 11 cm to 15 cm long from the top stem leaf to the base of an inflorescence; branched with 1 to 3 inflorescences per stem; diameter growing to 10 mm wide near the inflorescence; strigose; Yellow Green 147C.

*Size*.—Grows to 11 cm wide and 5.5 cm deep as disc enlarges.

*Form*.—Ray florets held slightly reflexed, mature disc is conic.

*Immature inflorescence*.—Grows to 2.8 cm wide and 2.5 cm deep, ray florets held at a 70 degree angle from the vertical and rolled up so only the back color shows, Yellow 4D with the tips Yellow 1B, disc color Yellow Green 146A.

*Ray florets*.—Without pistil or stamen, about 33 in number, grow to 45 mm long and 25 mm wide, tubular with a fan with 3 to 4 lobes, glabrous inside and out, tube 10 mm to 25 mm long and 1.5 mm to 4 mm wide, fan 12 mm to 30 mm long and 12 mm to 25 mm wide, margins entire, lobes 5 mm to 18 mm long and 1.5 mm to 4 mm wide, color inside and outside on tube and fan Yellow 11D, except tube base, Yellow Green 144A, and lobe margins on inside, Yellow 11A, ovary 5 mm long and 2 mm wide, White 155A with top Yellow Green 144A.

*Disc*.—Flat becoming conic, growing to 21 mm deep and 45 mm wide with maturity, Orange 24A where only bracts show and Yellow Green 146C where disc florets are open.

*Disc florets*.—About 400 in number, each with 1 pistil and 4 stamen, grow to 12 mm long and 3 mm wide, each with one persistent, very stiff linear bract (14 mm long with top ⅓ Orange 24A, middle ⅓ Yellow Green 146B, bottom ⅓ White 155A); corollas 7 mm long and 3 mm wide, tubular with 5 lobes, lobes flaring, 1 mm long and 1 mm wide with margin entire, tips acute, glabrous on both sides, both sides Yellow Green 146C; pistil 12 mm long, ovary 4 mm long, White NN155A, style 7 mm long Green White 157D, 2-branched stigma 1 mm long and spreading 2 mm, Green White 157A; stamen 5 mm long, filaments 2 mm long, threadlike, White 155A, anthers 3 mm long Brown 200A, pollen Orange 24B.

*Phyllaries*.—In 4 leafy series, area grows to 40 mm wide and 10 mm deep, lobes lanceolate in shape, reflexed, grow to 10 mm long and 3 mm wide, Green N137A, margins strigose, tip acute, strigose on both sides.

*Receptacle*.—Grows to 18 mm wide and 12 mm deep, White NN155B.

*Bloom period*.—July through October in Canby, Oreg.

*Fragrance*.—Floral.

*Lastingness*.—Each inflorescence lasts about two weeks in Canby, Oreg.

*Seeds*.—Not seen.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

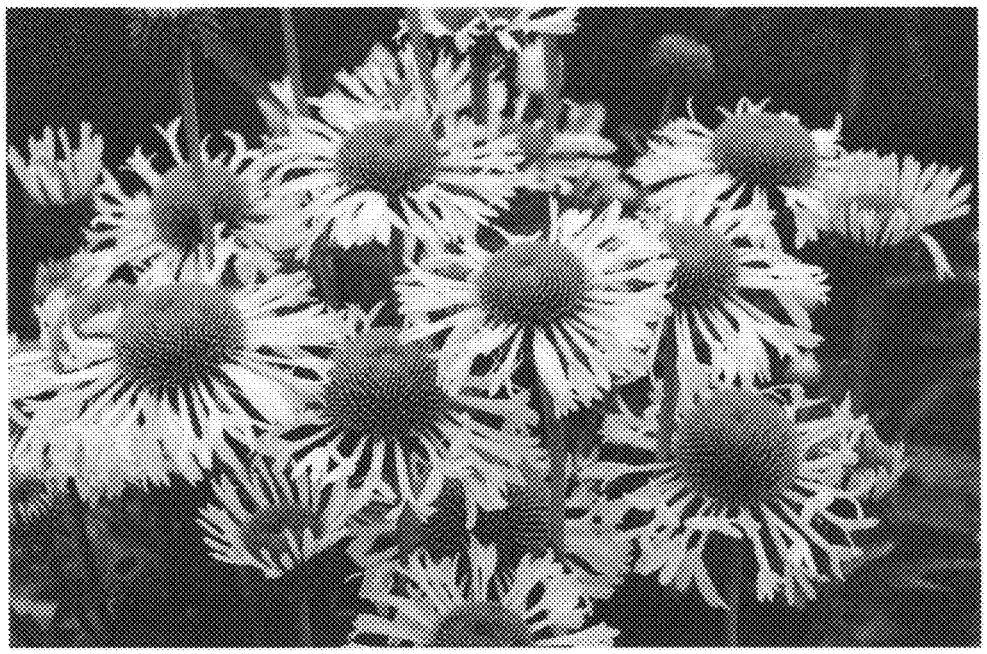

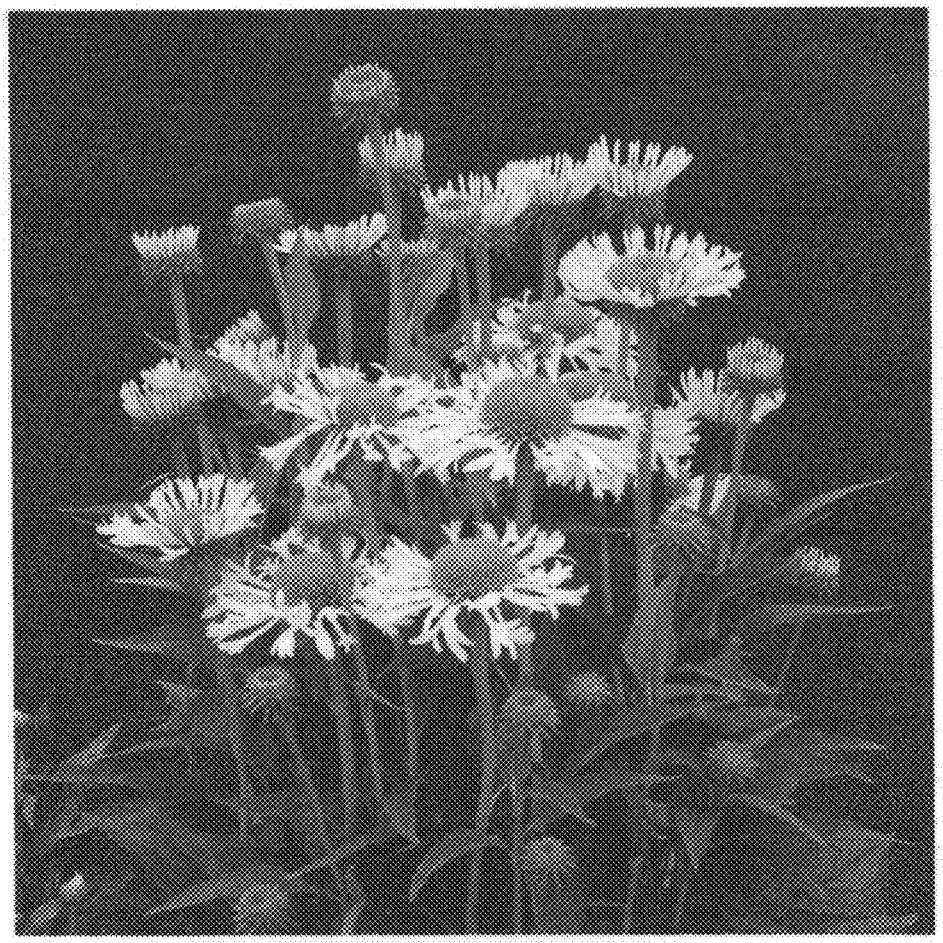
FIG. 1 above, FIG. 2 below